United States Patent
Brengartner

(10) Patent No.: US 10,571,380 B2
(45) Date of Patent: Feb. 25, 2020

(54) VIBRONIC SENSOR

(71) Applicant: Endress+Hauser GmbH+Co. KG, Maulburg (DE)

(72) Inventor: Tobias Brengartner, Emmendingen (DE)

(73) Assignee: Endress+Hauser SE+Co. KG, Maulburg (DE)

( * ) Notice: Subject to any disclaimer, the term of this patent is extended or adjusted under 35 U.S.C. 154(b) by 241 days.

(21) Appl. No.: 15/553,891

(22) PCT Filed: Jan. 29, 2016

(86) PCT No.: PCT/EP2016/051935
§ 371 (c)(1),
(2) Date: Aug. 25, 2017

(87) PCT Pub. No.: WO2016/134915
PCT Pub. Date: Sep. 1, 2016

(65) Prior Publication Data
US 2018/0031460 A1 Feb. 1, 2018

(30) Foreign Application Priority Data
Feb. 27, 2015 (DE) .................. 10 2015 102 834

(51) Int. Cl.
*G01N 9/00* (2006.01)
*G01N 11/10* (2006.01)
*G01N 11/00* (2006.01)

(52) U.S. Cl.
CPC ............. *G01N 9/002* (2013.01); *G01N 11/10* (2013.01); *G01N 2011/0073* (2013.01)

(58) Field of Classification Search
CPC ...... G01N 9/002; G01N 11/16; G01N 29/022; G01N 2009/006; G01N 2291/02818; G01F 23/28; G01F 23/296; G01F 23/2966

(Continued)

(56) References Cited

U.S. PATENT DOCUMENTS

| 5,323,633 | A | 6/1994 | Langdon |
| 5,323,638 | A | 6/1994 | Langdon |

(Continued)

FOREIGN PATENT DOCUMENTS

| CN | 1100805 A | 3/1995 |
| CN | 1473264 A | 2/2004 |

(Continued)

OTHER PUBLICATIONS

Search Report for GermanPatent ApplicationNo, 10 2015 102 834.4, German Patent Office, dated Dec. 12, 2015, 4 pp.

(Continued)

*Primary Examiner* — Benjamin R Schmitt
(74) *Attorney, Agent, or Firm* — Christopher R. Powers; PatServe

(57) ABSTRACT

Vibronic sensor and method of operation for monitoring the density and/or the viscosity of a medium in a container, comprising a mechanically oscillatable unit, a driving/receiving unit and an electronics unit, wherein the driving/receiving unit is embodied, using an electrical exciter signal, to excite the mechanically oscillatable unit to execute mechanical oscillations, and to receive the mechanical oscillations and to convert them into an electrical, received signal, wherein the electronics unit is embodied to produce the exciter signal such that a predeterminable phase shift is present between the exciter signal and received signal, wherein the electronics unit is embodied to set a first (Continued)

predeterminable phase shift and a second predeterminable phase shift, and to ascertain a first frequency and a second frequency corresponding to the predeterminable phase shifts, and to determine from the two frequencies the density and/or the viscosity of the medium using a first and/or second analytical formula.

12 Claims, 2 Drawing Sheets

(58) Field of Classification Search
USPC .............................................. 73/32 A, 290 V
See application file for complete search history.

(56) References Cited

U.S. PATENT DOCUMENTS

| | | | |
|---|---|---|---|
| 2008/0243400 A1* | 10/2008 | Bell | ...................... G01F 1/8413 |
| | | | 702/45 |
| 2016/0059153 A1* | 3/2016 | Smith | .................. B01D 21/245 |
| | | | 210/744 |
| 2017/0030870 A1* | 2/2017 | Dual | ...................... G01N 11/16 |

FOREIGN PATENT DOCUMENTS

| | | |
|---|---|---|
| CN | 101109686 A | 1/2008 |
| CN | 101517382 A | 8/2009 |
| CN | 102575956 A | 7/2012 |
| CN | 103080706 A | 5/2013 |
| CN | 103180695 A | 6/2013 |
| DE | 69504815 T2 | 2/1999 |
| DE | 10050299 A1 | 4/2002 |
| DE | 102012113045 A1 | 6/2014 |
| WO | 2014179050 A1 | 11/2014 |

OTHER PUBLICATIONS

Search Report for International Patent Application No. PCT/EP2016/051935, WIPO, dated Apr. 26, 2016. 12 pp.

* cited by examiner

VIBRONIC SENSOR

CROSS-REFERENCE TO RELATED APPLICATIONS

The present application is related to and claims the priority benefit of German Patent Application No. 10 2015 102 834.4, filed on Feb. 27, 2015 and International Patent Application No. PCT/EP2016/051935 filed on Jan. 29, 2016 the entire contents of which are incorporated herein by reference.

TECHNICAL FIELD

The invention relates to a vibronic sensor for determining and/or monitoring at least one process variable of a medium as well as to a method for operating the vibronic sensor.

BACKGROUND

Vibronic sensors are widely applied in process and/or automation technology. In the case of fill-level measuring devices, they comprise at least one mechanically oscillatable unit, such as, for example, an oscillatory fork, single rod or membrane. Such is excited during operation by means of a driving/receiving unit, frequently in the form of an electromechanical transducer unit, to execute mechanical oscillations. The electromechanical transducer unit can be, for example, a piezoelectric drive or an electromagnetic drive. The mechanically oscillatable unit can, in the case of flow measuring devices, however, also be embodied as an oscillatable tube, through which the medium flows, such as, for example, in a measuring device working according to the Coriolis principle.

SUMMARY

Corresponding field devices are produced by the applicant in great variety and in the case of fill-level measuring devices, for example, sold under the marks, LIQUIPHANT and SOLIPHANT. The underpinning measuring principles are known from a large number of publications. The driving/receiving unit uses an electrical exciter signal to excite the mechanically oscillatable unit to execute mechanical oscillations. Going the other way, the driving/receiving unit can convert mechanical oscillations received from the mechanically oscillatable unit into an electrical, received signal. The driving/receiving unit is either a separate driving unit and a separate receiving unit, or a combined driving/receiving unit.

In such case, the driving/receiving unit is often part of a feedback, electrical, oscillatory circuit, by means of which the exciting of the mechanically oscillatable unit to execute mechanical oscillations occurs. For example, for a resonant oscillation, the oscillatory circuit condition must be fulfilled, according to which the amplification factor is and all phases arising in the oscillatory circuit must sum to a multiple of 360°.

For exciting and fulfilling the oscillatory circuit condition, a certain phase shift between the exciter signal and the received signal must be assured. Therefore, frequently, a predeterminable value is tuned for the phase shift, thus a desired value for the phase shift between the exciter signal and the received signal. For this, a variety of solutions, both analog as well as also digital methods, are known from the state of the art. In principle, the tuning of the phase shift can be performed, for example, by using a suitable filter, or also be controlled by means of a control loop to a predeterminable phase shift, the desired value. Known, for example, from DE102006034105A1 is to use a tunable phase shifter. The additional integration of an amplifier with adjustable amplification factor for additional control of the amplitude of the oscillation is, in contrast, described in DE102007013557A1. DE102005015547A1 discloses the application of an allpass filter. The tuning of the phase shift is, moreover, possible by means of frequency search operation, such as disclosed, for example, in DE102009026685A1, DE102009028022A1, and DE102010030982A1. The phase shift can, however, also be controlled to a predeterminable value by means of a phase locked loop (PLL). An excitation method based on this is subject matter of DE00102010030982A1.

Both the exciter signal as well as also the received signal are characterized by their frequency f, amplitude A and/or phase $\phi$. Correspondingly, changes in these variables are usually taken into consideration for determining the process variables of interest, such as, for example, a predetermined fill level of a medium in a container, or also the density and/or viscosity of a medium or the flow of a medium through a pipe or tube. In the case of a vibronic limit level switch for liquids, it is distinguished, for example, whether the oscillatable unit is covered by the liquid or is freely oscillating. These two states, the free state and the covered state, are, in such case, distinguished, for example, based on different resonance frequencies, thus a frequency shift. The density and/or viscosity, in turn, can only be ascertained with such a measuring device, when the oscillatable unit is covered by the medium.

As described, for example, in DE10050299A1, the viscosity of a medium can be determined by means of a vibronic sensor based on the phase versus frequency curve ($\phi=g(f)$). This procedure is based on the dependence of damping of the oscillatable unit on the viscosity of the respective medium. In such case, the smaller the viscosity, the steeper is the slope of the phase versus frequency curve. In order to eliminate the influence of density on the measuring, the viscosity is determined based on a frequency change resulting from two different phase values, thus by means of a relative measurement. In this regard, either two different phase values can be set and the associated frequency change determined, or a predetermined frequency band is moved through and it is detected when at least two predetermined phase values are reached.

Known from DE102007043811A1 is, moreover, to ascertain from a change of the eigenfrequency and/or resonant frequency and/or phase a change of the viscosity and/or based on correspondingly furnished dependencies of the oscillations of the oscillatable unit on the viscosity of the respective medium to determine the viscosity. Also in the case of this procedure, the dependence of viscosity on the density of the medium must be taken into consideration.

Known from DE10057974A1 for determining and/or monitoring the density of a medium are a method as well as an apparatus, by means of which the influence of at least one disturbing variable, for example, the viscosity, on the oscillation frequency of the mechanically oscillatable unit can be ascertained and correspondingly compensated. Described in DE102006033819A1 is, furthermore, the setting of a predeterminable phase shift between the exciter signal and the received signal, in the case of which effects from changes of viscosity of the medium on the mechanical oscillations of the mechanically oscillatable unit are negligible. In such case, the density is determined essentially according to the formula $$\rho_{Med} = \frac{1}{K}\left[\left(\frac{f_{0,Vak} + C \cdot t + A \cdot t^2}{f_{r,P,Med}}\right)^2 \cdot (1 + D \cdot p) - 1\right]$$

wherein K is the density sensitivity of the mechanically oscillatable unit, $f_{0,Vak}$ the frequency of the mechanical oscillations in vacuum, C and A, respectively, the linear and quadratic temperature coefficients of the mechanically oscillatable unit, t the process temperature, $f_{0,Med}$ the frequency of the mechanical oscillations in the medium, D the pressure coefficient, and ρ the pressure of the medium.

With the empirically derived assumption that the measurement at a certain predeterminable phase shift is independent of viscosity, limitations for the applicability of the described measuring principles result. Thus, a maximum allowable viscosity of a particular medium must be determined, up to which the measuring principle for density determination enables, at all, an exact measurement.

Disadvantageous in the case of the mentioned apparatuses and methods is, on the one hand, that, for determining the viscosity of the medium, its density must be taken into consideration and vice versa. On the other hand, the various measuring principles are based on empirically ascertained relationships. From this, there result, in given cases, inaccuracies in the determining of density, and viscosity, as well as limitations for the possible areas of application.

Therefore, an object of the present invention is to expand the range of applications for determining the density and/or viscosity by means of a vibronic sensor.

This object is achieved by the features of the apparatus claim 1 as well as by the features of the method claim 10.

According to the invention, a vibronic sensor for determining and/or monitoring at least the density and/or the viscosity of a medium in a container is provided, comprising at least one mechanically oscillatable unit, a driving/receiving unit and an electronics unit. The driving/receiving unit is embodied by means of an electrical exciter signal to excite the mechanically oscillatable unit to execute mechanical oscillations, and to receive mechanical oscillations of the mechanically oscillatable unit and to convert them into an electrical, received signal. Furthermore, the electronics unit is embodied to produce the exciter signal, starting from the received signal, in such a manner that a predeterminable phase shift is present between the exciter signal and received signal, to set at least a first predeterminable phase shift and a predeterminable second phase shift, to ascertain first and second frequencies corresponding to the respective predeterminable phase shifts, and from the two frequencies to determine by means of a first analytical formula the density and/or by means of a second analytical formula the viscosity of the medium. Especially, the first and second phase shifts can be set alternately in predeterminable time intervals. The empirical basis of the density- and/or viscosity determination is thus replaced according to the invention by an analytical basis. Through this procedure, the interactions between the oscillatable unit and the medium are taken into consideration. According to the invention, for this, the electronics unit must be embodied for evaluation of the frequencies of the oscillatable unit at two different predeterminable phase shifts between the exciter signal and the received signal. The corresponding vibronic sensor is then universally applicable for all viscous media, in which the oscillatable unit can execute an oscillatory movement, and suitable to ascertain both the density as well as also the viscosity. Moreover, the solution of the invention increases the accuracy of the density and/or viscosity determination in comparison to the methods known from the state of the art, since a reciprocal influencing of the two variables, density and viscosity, is taken into consideration. This will be seen more clearly on the basis of the derivations below.

In an especially preferred embodiment, the first predeterminable phase shift amounts essentially to +/−90°, and the second predeterminable phase shift essentially to 45° or −135°. A phase shift of +/−90° corresponds to a resonant exciting of the oscillatable unit corresponding to the fundamental oscillation mode. In such case, a purely mechanical oscillator in the case of a first predeterminable phase shift of −90° executes resonant mechanical oscillations. Correspondingly, the second predeterminable phase shift would be −135°. Taking into consideration the phase shifts of an electronics unit and a driving/receiving unit, however, especially in the case of a LIQUIPHANT instrument sold by the applicant, an additional phase shift of +180° is produced, so that the first predeterminable phase shift must be +90° and the second predeterminable phase shift +45°.

It is, furthermore, advantageous, when the oscillatable unit is arranged in a defined position within the container, in such a manner that it extends to a determinable immersion depth in the medium.

Additionally, it is advantageous, when the electronics unit is embodied to determine and/or to monitor a predetermined fill level of the medium in the container.

In an embodiment, the oscillatable unit is a membrane, single rod or oscillatory fork.

In an embodiment, the driving/receiving unit includes a piezoelectric element. Alternatively, the driving/receiving unit is an electromagnetic driving/receiving unit.

In an especially preferred embodiment, the first analytical formula and/or the second analytical formula result from the solution of an equation of motion for an oscillatory movement of the oscillatable unit, taking into consideration the interaction of the oscillatable unit with the medium in the form of a compressive force and a frictional force, which arise from the medium surrounding the oscillatable unit, as well as a frictional force, which arises as a result of an equally formed movement of the oscillatable unit within the medium. Due to the goal of obtaining an analytical solution of the equation of motion, the oscillatory movement, which in reality corresponds to a bending oscillation, is approximated by a torsional oscillation. Furthermore, there serves as an approximation of the geometry of the oscillatable unit for each of the two fork tines two elliptical cylinders of different dimensions.

It is then advantageous, when the electronics unit is embodied to calculate the density essentially according to the formula $$\rho = -\frac{T_2 + T_6 + \sqrt{T_3 + T_4}}{\hat{B}_a T_5}$$

and/or to calculate the viscosity according to the formula $$\eta = \frac{T_1 + \omega_{135}(T_2 - \sqrt{T_3 + T_4})}{\hat{C}_a T_5},$$

wherein $T_1 = -2\hat{B}_a \hat{C}_a \omega_{90}^2 (\gamma \omega_{135} \omega_{90}^2 + D_r(T)(-\omega_{135}^2 + \omega_{90}^2))$, $T_2 = \hat{A}_a^2 D_r(T) \omega_{90}^3 - \hat{A}_a^2 \gamma \omega_{135} \omega_{90}^3 - \hat{A}_a^2 \theta \omega_{135}^2 \omega_{90}^3$, $$T_3 = \hat{A}_a^2 \omega_{90}{}^3 \hat{A}_a^2 (D_r(T) + \omega_{135}(\gamma - \Theta\omega_{135}))^2 \omega_{90}{}^2,$$

$$T_4 = \hat{A}_a^2 \omega_{90} 4 \hat{B}_a \hat{C}_a \omega_{135}(D_r(T) - \Theta\omega_{90}{}^2)(-\gamma\omega_{135}\omega_{90}{}^2 + D_r(T)(\omega_{135}{}^2 - \omega_{90}{}^2)),$$

$$T_5 = 2\omega_{135}\omega_{90}{}^3 (-\hat{A}_a^2 \omega_{135} + \hat{B}_a \hat{C}_a \omega_{90}), \text{ and}$$

$$T_6 = 2\hat{B}_a \hat{C}_a \omega_{135}\omega_{90}{}^2 (-D_r(T) + \Theta\omega_{90}{}^2),$$

wherein $\ominus$ is the mass moment of inertia of the oscillatory rods of the oscillatable unit in the state not covered by medium, wherein $\omega_0$ is the angular frequency of the oscillatable unit in the undamped case, wherein $D_r(T)$ is the temperature dependent torsional stiffness of the membrane, wherein $\gamma$ is the damping of the oscillatable unit not covered with medium, wherein $\hat{A}_a$, $\hat{B}_a$ and $\hat{C}_a$ are geometry dependent parameters, and wherein $\omega_{90}$ and $\omega_{135}$ are the frequencies corresponding to predeterminable phase shifts of essentially $+/-90°$ and $45°$ or $-135°$ between the exciter signal and the received signal.

For the angular frequency of the oscillatable unit, an oscillatable unit in vacuum at defined temperature was assumed for the analytical derivation. Practically, however, the damping in air can be neglected, so that for the "undamped case" in the following it is assumed that the oscillatable unit is not covered by medium. The damping of the oscillatable unit not covered with medium describes, in principle, the intrinsic damping of the oscillatable unit. Again for this, the damping by air is neglected in the following. In these formulas, the pressure dependence in the case of determining density and/or viscosity is not used in the analytical model. It is, however, taken into consideration by an empirically ascertained polynomial, similarly as in the case of the methods according to the state of the art.

Regarding the method, the object of the invention is achieved by a method for determining density and/or viscosity of a medium in a container by means of a vibronic sensor, especially by means of a sensor according to at least one of the preceding claims, wherein an oscillatable unit is excited by means of an electrical exciter signal to execute mechanical oscillations, and mechanical oscillations of the mechanically oscillatable unit are received and converted into an electrical, received signal, and wherein the exciter signal is produced, starting from the received signal, in such a manner that a predeterminable phase shift is present between the exciter signal and the received signal. According to the invention, at least a first predeterminable phase shift and a second predeterminable phase shift are set, wherein first and second frequencies corresponding to the respective predeterminable phase shifts are ascertained, and wherein from the two frequencies the density of the medium is determined by means of a first analytical formula and/or the viscosity of the medium is determined by means of a second analytical formula.

In such case, it is advantageous, when essentially $+/-90°$ is set as the first predeterminable phase shift, and essentially $45°$ or $-135°$ as the second predeterminable phase shift.

An embodiment provides that a predetermined fill level of the medium is monitored in the container.

An especially preferred embodiment provides that the first analytical formula and/or the second analytical formula result from the solution of an equation of motion for an oscillatory movement of the oscillatable unit, in the case of whose formation the interaction of the oscillatable unit with the medium as expressed by a compressive force and a frictional force, which result from the medium surrounding the oscillatable unit, as well as a frictional force, which arises as a result of an equally formed movement of the oscillatable unit within the medium, are taken into consideration. Toward the goal of obtaining an analytical solution of the equation of motion, the oscillatory movement, which corresponds in reality to a bending oscillation, is approximated by a torsional oscillation. Furthermore, two elliptical cylinders of different dimensions serve as an approximation of the geometry of the oscillatable unit, namely one set for each of the two fork tines. Here, it is noted that, without limitation to the generality, also any other geometry can be selected for the oscillatable unit. In such case, however, the geometric coefficients must be correspondingly adapted.

It is then advantageous, when essentially the density is calculated according to the formula $$\rho = -\frac{T_2 + T_6 + \sqrt{T_3 + T_4}}{\hat{B}_a T_5}$$

and/or the viscosity according to the formula $$\eta = \frac{T_1 + \omega_{135}(T_2 - \sqrt{T_3 + T_4})}{\hat{C}_a T_5},$$

wherein $$T_1 = -2\hat{B}_a \hat{C}_a \omega_{90}{}^2 (\gamma\omega_{135}\omega_{90}{}^2 + D_r(T)(-\omega_{135}{}^2 + \omega_{90}{}^2)),$$

$$T_2 = \hat{A}_a^2 D_r(T)\omega_{90}{}^3 - \hat{A}_a^2 \gamma\omega_{135}\omega_{90}{}^3 - \hat{A}_a^2 \Theta\omega_{135}{}^2 \omega_{90}{}^3,$$

$$T_3 = \hat{A}_a^2 \omega_{90}{}^3 \hat{A}_a^2 (D_r(T) + \omega_{135}(\gamma - \Theta\omega_{135}))^2 \omega_{90}{}^2,$$

$$T_4 = \hat{A}_a^2 \omega_{90} 4 \hat{B}_a \hat{C}_a \omega_{135}(D_r(T) - \Theta\omega_{90}{}^2)(-\gamma\omega_{135}\omega_{90}{}^2 + D_r(T)(\omega_{135}{}^2 - \omega_{90}{}^2)),$$

$$T_5 = 2\omega_{135}\omega_{90}{}^3 (-\hat{A}_a^2 \omega_{135} + \hat{B}_a \hat{C}_a \omega_{90}), \text{ and}$$

$$T_6 = 2\hat{B}_a \hat{C}_a \omega_{135}\omega_{90}{}^2 (-D_r(T) + \Theta\omega_{90}{}^2),$$

wherein $\ominus$ is the mass moment of inertia of the oscillatory rods of the oscillatable unit in the state not covered by medium, wherein $\omega_0$ is the angular frequency of the oscillatable unit in the undamped case, wherein $D_r(T)$ is the temperature dependent torsional stiffness of the membrane, wherein $\gamma$ is the damping of the oscillatable unit not covered with medium, wherein $\hat{A}_a$, $\hat{B}_a$ and $\hat{C}_a$ are geometry dependent parameters, and wherein $\omega_{90}$ and $\omega_{135}$ are the frequencies corresponding to predeterminable phase shifts of essentially $+/-90°$ and $45°$ or $-135°$ between the exciter signal and the received signal.

Summarizing, the present invention provides the following advantages compared to the state of the art:

The density can be ascertained independently of the viscosity of the medium, the viscosity can be ascertained independently of the density of the medium, and the analytical formulas of the invention for the density and/or viscosity are more exact than the formulas known from the state of the art.

BRIEF DESCRIPTION OF THE DRAWINGS

The invention as well as advantageous embodiments thereof will now be described in greater detail based on the appended drawing, the figures of which show as follows.

DETAILED DESCRIPTION

Figure 1:
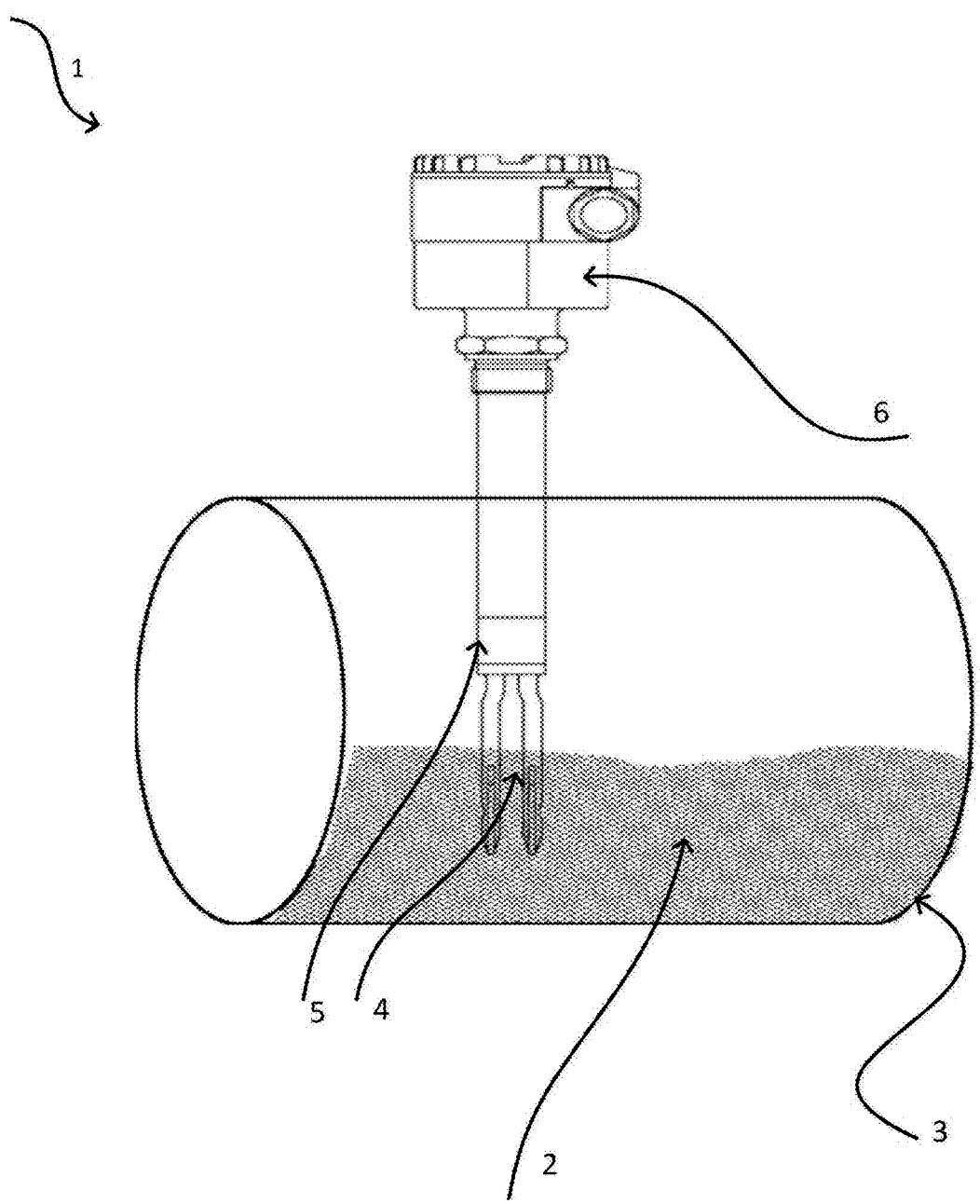
FIG. 1 shows a schematic drawing of a vibronic sensor according to state of the art.

FIG. 1 shows a vibronic sensor 1. Included in the vibronic sensor 1 is an oscillatable unit 4 in the form of an oscillatory fork, which extends partially into a medium 2, which is located in a container 3. The oscillatable unit is excited to execute mechanical oscillations by means of the exciter/receiving unit 5, which can be, for example, a piezoelectric stack- or bimorph drive. It is understood, however, that also other embodiments of a vibronic sensor fall within the scope of the invention. Furthermore, an electronics unit 6 is shown, by means of which the signal registration, -evaluation and/or feeding occurs.

Figure 2:
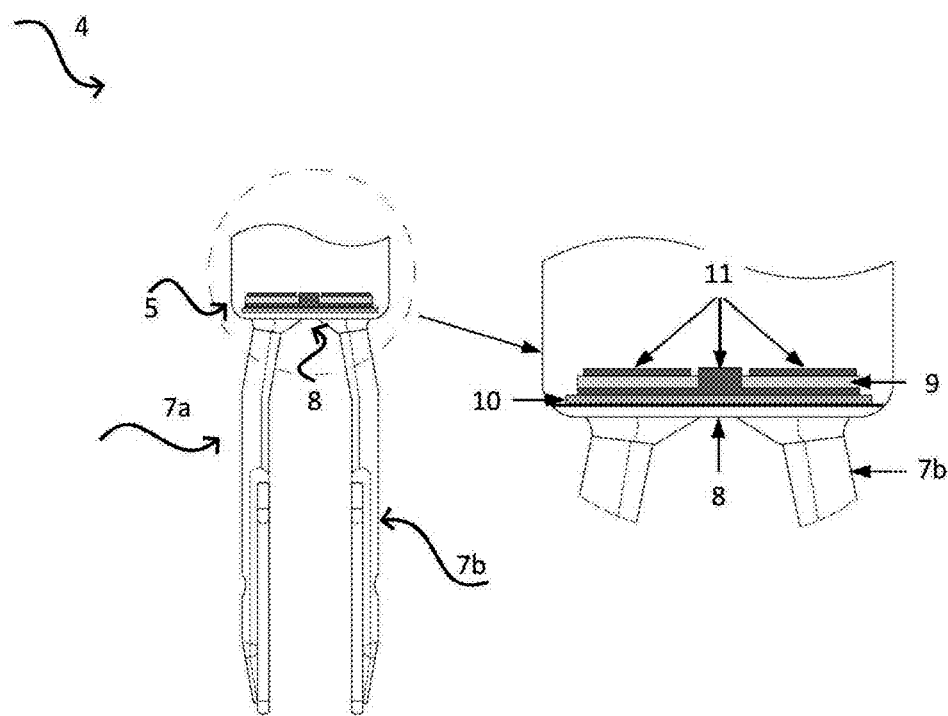
FIG. 2 shows a schematic drawing of an oscillatory fork.

FIG. 2 shows an oscillatable unit 4 in the form of an oscillatory fork, such as is integrated, for example, into the vibronic sensor 1 sold by the applicant under the mark, LIQUIPHANT. Oscillatory fork 4 includes two oscillatory rods 7a, 7b, also called fork tines, mounted on a membrane 8. In order to cause the oscillatory rods 7a, 7b to execute mechanical oscillations, a driving/receiving unit 5 mounted by material bonding on the side of the membrane 8 facing away from the rods 7a, 7b exerts a force on the membrane 8. The driving/receiving unit 5 is an electromechanical transducer unit, and comprises, for example, a piezoelectric element 9, or also an electromagnetic drive. The drive unit 5 and the receiving unit are constructed as two separate units, or as a combined driving/receiving unit. In the detail drawing on the right side of FIG. 2, the driving/receiving unit 5 is shown in detail. A piezoelectric element 9 is arranged on a steatite disk 10 and equipped with electrodes 11 for applying the exciter signal as well as for tapping the received signal.

In the case, in which the driving/receiving unit 5 includes a piezoelectric element 9, the force applied to the membrane 8 is generated by applying an exciter signal $U_E$, for example, in the form of an electrical, alternating voltage. A change of the applied electrical voltage effects a change of the geometric shape of the driving/receiving unit 5, thus a contraction or expansion of the piezoelectric element 9, in such a manner that the applying of an electrical, alternating voltage in the form of exciter signal $U_E$ brings about an oscillation of the membrane 8 connected by material bonding with the driving/receiving unit 5.

As indicated above, a goal of the present invention is to expand the range of applications for determining density and/or viscosity by means of a vibronic sensor 1. Previously, the methods for determining density and/or viscosity have been based on empirically ascertained assumptions. According to the invention, these empirical models are replaced by an analytical model for describing the oscillatory movements of a vibronic sensor 1 in a viscous medium. Such a model has not previously been available. Therefore, the bases of this model will now be briefly explained.

Under the assumption of an ideal drive unit 5, the oscillatable unit 4 can be described as a harmonic, single-mass oscillator. The oscillatory movements of the two oscillatory rods 7a, 7b, or fork tines, correspond largely to the deflections of a bending beam. Due to the usually much more complex geometric structure of the oscillatable unit 4 of a vibronic sensor 1, it is, however, helpful to approximate the oscillatory movements of the two oscillatory rods 7a, 7b by a rotational movement. Differences between the mathematical description and the actual oscillatory movements resulting from the approximation can be eliminated a posteriori by taking suitable correction terms into consideration.

The equation of motion for a free, forced oscillation of an oscillatable unit 4 such as in FIG. 2 in the form of a rotational movement is, in principle, known from the state of the art and can be derived based on the moments acting on the two oscillatory rods 7a, 7b. If, supplementally, also the interactions between the fluid and the oscillatable unit are taken into consideration, there results as equation of motion a second order differential equation:

$$M_S + M_D + M_R + M_F = M_E$$

$$\Theta\ddot{\phi}(t) + \gamma\dot{\phi}(t) + D_r\phi(t) + M_F = \phi_0 D_r\sin(\omega t).$$

In such case, describes $M_F$ the moment due to the fluid-structure interaction, $M_E$ the exciter moment, $M_R$ the moment from the stiffness of the membrane, $M_D$ the moment due to the inner damping of the oscillatable unit and $M_S$ the moment due to the mass moment of inertia of the fork tines. Furthermore, $\phi$ is the deflection, or in the here considered approximation the rotational angle, of the oscillatory rods 7a,7b of the oscillatable unit 4 from the rest position, $\Theta$ the mass moment of inertia brought about by the mass of the oscillating oscillatory rods 7a,7b, $\gamma$ the damping coefficient resulting from the inner damping of the oscillatable unit 4 and $D_r$ the torsional stiffness due to the stiffness of the membrane 8.

A particular solution results by means of the ansatz $\phi(t)=\phi_0 V\sin(\omega t+\phi)$, with the amplification function $$V(\omega) = \frac{1}{\sqrt{4D^2\left(\frac{\omega}{\omega_0}\right)^2 + \left(1 - \left(\frac{\omega}{\omega_0}\right)^2\right)^2}},$$

which describes the amplitude behavior of the oscillatable unit 4, and with the phase of the oscillatable unit 4 obeying $$\tan\varphi = \frac{2D\omega\omega_0}{\omega^2 - \omega_0^2}.$$

In such case, $$D = \frac{\gamma}{2\Theta\omega_0},$$

the damping ratio or Lehr, which represents a characteristic variable for the quality of the oscillatory system, and $$\omega_0 = \sqrt{\frac{D_r}{\Theta}},$$

the eigenfrequency of the corresponding undamped oscillator.

The moment $M_F$ due to the fluid-structure interaction is dependent on the geometry of the oscillatable unit 4 and describes, in principle, the interaction between the oscillatable unit 4 and the relevant medium 2. The case $M_F=0$ describes the case of an oscillation of the oscillatable unit 4 outside of the medium 2.

Figures 3A, 3B, 3C:
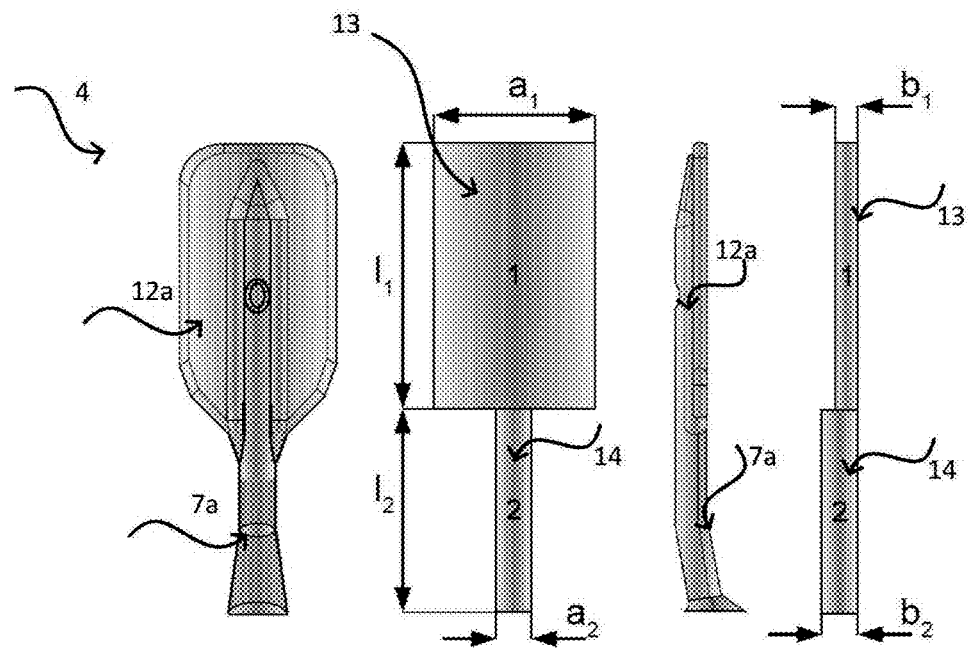
FIG. 3 shows an illustration of the approximation of the geometry of oscillatory forks using elliptical cylinders.

An analytical solution of the equation of motion can only be obtained by assuming simple geometrical structures for the oscillatable unit 4, such as, for example, a sphere (see also W. Y. Shih, X. Li, H. Gu, W. H. Shih and I. A. Aksay: "Simultaneous liquid viscosity and density determination with piezoelectric unimorph cantilevers", published in Journal of Applied Physics, 89(2):1497-1505, 15. 1 in the year 2001, a cuboid-shaped structure (see also J. E. Sader: "Frequency response of cantilever beams immersed in viscous fluids with applications to the atomic force microscope", published in the Journal of Applied Physics, 84(1): 64-76,1. 7 in the year 1998 or an infinitely extended circular cylinder (see also the Dissertation of W. Zhang: Energy Dissipations in MEMS Resonators: Fluid Damping of Flexura Resonators and Thermoelastic Damping, published December 2006 at the University of California). These geometries do not really suit the much more complex geometry of the oscillatable unit 4, for example, in the form of an oscillatory fork of a vibronic sensor 1. Much better suited for an oscillatory fork is the geometry of an elliptical cylinder with the semi axes a and b, such as, for example, in the dissertation of J. Friedmann, Untersuchungen über das Verhalten der Schwingfrequenz bei Stimmgabelgasdichtemessgeräten (Investigations concerning the behavior of oscillation frequency in the case of tuning fork gas density measuring devices, at the University Fridericiana Karlsruhe (Technical Hochschule) at the Faculty for Elektrotechnik, January 1976. Using this approximation, the real dimensions of the oscillatory rods 7a, 7b of the oscillatable unit 4 enter advantageously into the analytical solution. This approximation of the geometry for the oscillatable unit 4 is illustrated in FIG. 3. For the oscillatory fork 4 applied in the LIQUIPHANT instrument, a paddle 12a, 12b is formed terminally on each of the two oscillatory rods 7a, 7b, this being shown in FIG. 3a. In order to take this into consideration, the geometry of the oscillatable unit is approximated by two elliptical cylinders for each oscillatory rod, such as illustrated in FIG. 3b. The first elliptical cylinder 13 of length $l_1$, width $a_1$ as well as thickness $b_1$ serves to represent the paddles 12a, 12b, while the second elliptical cylinder 14 of length $l_2$, width $a_2$ as well as thickness $b_2$ represents the oscillatory rods 7a, 7b. FIG. 3c shows a fork tine 7a of the oscillatory fork 4 as well as the approximated geometry with the two elliptical cylinders 13,14 in side view.

The interaction between the oscillatable unit 4 and the medium 2 arises as a result of the medium 2 being moved by the movement of the oscillatable unit 4 in the immersed state. This has the result that forces $F_F$ occur opposing the movement of the oscillatable unit 4. These can be subdivided into compressive forces and frictional forces, i.e.:

$$F_F = F_C + F_R F_{SP}.$$

In such case, $F_C$ is the compressive force, $F_R$ the frictional force acting due to the fluid surrounding the oscillating, elliptical cylinder, and $F_{SP}$ a frictional force acting supplementally as a result of the equally formed movement of an elliptical cylinder. In order to calculate these forces, the velocity distribution of the medium 2 in the environment of the oscillatable unit 4 must be known. For this, reference is made to the "Lehrbuch der Hydrodynamik" (hydrodynamics textbook) by H. Lamb, Vol. 26 of B. G. Teubner's collection of mathematical science textbooks including applications, B. G. Teubner, publisher, Leipzig and Berlin, 3rd edition of 1907.

Based on the textbook "Hydrodynamik" (hydrodynamics), Vol. 6, of the series, Lehrbuch der Theoretischen Physik (textbooks of theoretical physics), by L. D. Landau and E. M Lifschitz, Akademie Verlag, publishers, Berlin, 5th edition of 1991, the velocity distribution can be divided into a normal and a tangential component. While the normal velocity component is not influenced by the viscosity of the medium 2, it can be determined based on the model of an ideal fluid. The tangential component, in contrast, in the region around the oscillatable unit 4 is influenced by the viscosity of the medium. In the limiting case of infinite distance from the oscillatable unit 4, in contrast, the normal component transforms into the tangential velocity component.

Taking into consideration the geometry of an elliptical cylinder 13,14 and using the basic hydrodynamic equations, Euler's equation, the continuity equation, as well as Thomson's theorem and d'Alembert's paradox, the compressive force $F_C$ per unit length, which acts on an elliptical cylinder 13,14, can be determined as follows:

$$F_C = \rho a^2 \pi \frac{du}{dt},$$

wherein $\rho$ is the density of the medium 2 and u the velocity of the oscillatable unit 4.

The frictional force $F_R$, which acts due to the fluid surrounding the oscillating, elliptical cylinder, can be derived starting from the frictional force $F_y$, which acts on an infinitely extended, planar area $$F_y = \eta \frac{\partial \vec{v}_y}{\partial x}\bigg|_{x=0},$$

and results as:

$$F_R = 2\sqrt{2}\, bX\left(\frac{b}{a}\right)\left(\sqrt{\omega \rho \eta}\, u + \sqrt{\frac{\rho \eta}{\omega}}\frac{du}{dt}\right),$$

with the oscillation frequency $\omega$, and the function $$X\left(\frac{b}{a}\right) = \frac{EI_1\left[1 - \frac{1}{(b/a)^2}\right] - EI_2\left[1 - \frac{1}{(b/a)^2}\right]}{\frac{b}{a}\left(\left(\frac{b}{a}\right)^2 - 1\right)},$$

wherein $EI_1$ and $EI_2$ refer to the complete elliptic integrals of first and second order.

The function $$X\left(\frac{b}{a}\right)$$

can be approximated by an exponential function.

The force $F_{SP}$ acting supplementally as a result of the equally formed movement of an elliptical cylinder is a result of the Stoke's frictional force. It is independent of the oscillation frequency ω and proportional to the viscosity η of the medium. Based on the dissertation, "Energy Dissipations in MEMS Resonators: Fluid Damping of Flexural Resonators and Thermoelastic Damping" of W. Zhang as well as the "Lehrbuch der Hydrodynamik" of H. Lamb, there results for the frictional force $F_{SP}$ $$F_{SP} = \frac{4\pi\eta}{\frac{b}{a+b} - \gamma_E - \log\left(\frac{Re \cdot (a+b)}{16a}\right)} \cdot u,$$

with the Euler constant $\gamma_E \approx 0.577$ and the Reynolds number Re, a dimensionless, characteristic variable for the flow of a medium 2.

In order to obtain the equation of motion describing the oscillatory movement of an oscillatable unit in a viscous medium, the entire force per length unit $F_F$ acting on the oscillatable unit due to the interaction between the oscillatable unit and the medium must be converted into the associated moment $M_F$. In such case, it must be taken into consideration that each of the oscillatory rods was approximated by two elliptical cylinders of different dimensions, such as described in connection with FIG. 3.

There then results for the equation of motion for the oscillatory movement of the oscillatable unit 4 in a viscous medium 2

$$(\Theta + \hat{\Theta}_F)\ddot{\phi}(t) + (\gamma + \hat{\gamma}_F)\dot{\phi}(t) + D_r\phi(t) = M_E \sin(\omega t),$$

wherein $\hat{\Theta}_F$ is the supplementally coupling, mass moment of inertia and $\hat{\gamma}_F$ the supplementally acting, torsional damping due to the interaction of the oscillatable unit 4 with the medium 2. For these terms, the already mentioned, numerically ascertainable, correction terms are available for matching the equation of motion to a bending oscillation. The correction terms can be calculated, for example, from a comparison of the deflections of the oscillatable unit 4 in the case of a bending oscillation and in the case of a torsional oscillation by means of the ANSYS simulation tool.

A particular solution for this differential equation of second order can be won of the form $$\phi(t) = \phi_0 V(\omega) \sin(\omega t + \varphi(\omega))$$

wherein $V(\omega)$ is the so-called amplification function, which represents the amplitude behavior of the oscillatable unit 4, and $\varphi(\omega)$ the phase difference of the oscillatable unit 4. The equation of motion for an oscillatable unit 4 oscillating in a viscous medium 2 differs, thus, clearly from that in the uncovered case, such as described above. The oscillatory movements of the oscillatable unit 4 depend in the case of the immersion in a viscous medium 2 on, besides the density ρ and viscosity η, also the oscillation frequency ω of the oscillatable unit 4.

The oscillatory movement of a vibronic sensor 1 in a viscous medium 2 is that of a time variable oscillatory system. The mass coupling by the viscous medium 2 depends, in such case, on changes of the density ρ and/or viscosity η. The mass coupling is additionally dependent on the oscillation frequency ω of the oscillatable unit 4. It is thus, strictly speaking, not possible to characterize a vibronic sensor 1 using a constant eigenfrequency or a constant Lehr's damping ratio.

By evaluation of the oscillation frequency at a phase shift between exciter signal $U_E$ and received signal $U_R$ of essentially +/−90° and 45° or −135°, the already mentioned analytical formulas for the density and the viscosity can be ascertained:

$$\eta = \frac{T_1 + \omega_{135}(T_2 - \sqrt{T_3 + T_4})}{\hat{C}_a T_5}, \text{ and}$$

$$\rho = -\frac{T_2 + T_6 + \sqrt{T_3 + T_4}}{\hat{B}_a T_5}.$$

In such case, the following relationships hold:

$T_1 = -2\hat{B}_a\hat{C}_a\omega_{90}^2(\gamma\omega_{135}\omega_{90}^2 + D_r(T)(-\omega_{135}^2 + \omega_{90}^2)),$ $T_2 = \hat{A}_a^2 D_r(T)\omega_{90}^3 - \hat{A}_a^2\gamma\omega_{135}\omega_{90}^3 - \hat{A}_a^2\Theta\omega_{135}^2\omega_{90}^3,$ $T_3 = \hat{A}_a^2\omega_{90}^3 \hat{A}_a^2(D_r(T) + \omega_{135}(\gamma - \Theta\omega_{135}))^2\omega_{90}^2,$ $T_4 = \hat{A}_a^2\omega_{90}4\hat{B}_a\hat{C}_a\omega_{135}(D_r(T) - \Theta\omega_{90}^2)(-\gamma\omega_{135}\omega_{90}^2 + D_r(T)(\omega_{135}^2 - \omega_{90}^2)),$ $T_5 = 2\omega_{135}\omega_{90}^3(-\hat{A}_a^2\omega_{135} + \hat{B}_a\hat{C}_a\omega_{90}),$ and $T_6 = 2\hat{B}_a\hat{C}_a\omega_{135}\omega_{90}^2(-D_r(T) + \Theta\omega_{90}^2),$ Here, Θ is the mass moment of inertia of the oscillatory rods of the oscillatable unit in the state, not covered by medium, as calculated, for example, by means of the ANSYS software. Furthermore, $\omega_0$ and $D_r(T)$ can be measured. The damping y of the oscillatable unit not covered with medium can, finally, be calculated by measuring Lehr's damping ratio and is, in given cases, even negligible. The geometry dependent parameters $\hat{A}_a$, $\hat{B}_a$ and $\hat{C}_a$ can, finally, be calculated, for example, by means of a so-called parameter estimation method, such as, for example, described in DE102012113045A1 or in the previously unpublished application DE102013106172.9. The frequencies $\omega_{90}$ and $\omega_{135}$ are then the frequencies measured during operation of the vibronic sensor at a predeterminable phase shift of essentially +/−90° and 45° or −135° between the exciter signal and the received signal.

LIST OF REFERENCE NUMBERS 1 vibronic sensor
2 medium
3 container
4 oscillatable unit
5 electromechanical transducer unit
6 electronics unit
7a, 7b oscillatory rods of the oscillatable unit
8 membrane
9 piezoelectric element
10 steatite disk
11 electrodes
12a, 12b paddles of the oscillatable unit
13 first elliptical cylinder
14 second elliptical cylinder
$U_E$ exciter signal
$U_R$ received signal
φ rotational angle of the oscillatory rods of the oscillatable unit from the resting position
Θ mass moment of inertia resulting from the mass of the oscillating oscillatory rods
γ damping coefficient resulting from the inner damping of the oscillatory system
$D_r$ torsional stiffness due to the stiffness of the membrane a,b semi axes of an elliptical cylinder
$l_i$ length of the elliptical cylinder
$a_i$ width of the elliptical cylinder
$d_i$ thickness of the elliptical cylinder
$F_C$ compressive force
$F_R$ frictional force due to the fluid surrounding the oscillating, elliptical cylinder
$F_{SP}$ supplemental frictional force acting as a result of the equally formed movement of an elliptical cylinder
$\rho$ density of the medium
u velocity of the oscillatable unit
$\omega$ oscillation frequency of the oscillatable unit
$\omega_0$ angular frequency of the oscillatable unit in the undamped case
$\gamma_E$ Euler's constant
Re Reynolds number
$\hat{\Theta}_F$ supplementally coupling, mass moment of inertia resulting from interaction with the medium
$\hat{\gamma}_F$ supplementally acting, torsional damping due to interaction of the oscillatable unit with the medium
$V(\omega)$ amplification function, which represents the amplitude behavior of the oscillatable unit
$\varphi(\omega)$ phase difference of the oscillatable unit
$\hat{A}_a, \hat{B}_a, \hat{C}_a$ geometry dependent parameters
$\omega_{90}, \omega_{135}$ frequencies corresponding to predeterminable phase shifts of 90° and 45°
$\varphi_{45}, \varphi_{90}$ predeterminable phase shifts of 45° and 90°

The invention claimed is:

1. A vibronic sensor for monitoring at least the density and/or the viscosity of a medium in a container, the sensor comprising:
 a mechanically oscillatable unit;
 a driving/receiving unit structured to excite the mechanically oscillatable unit using an electrical exciter signal to execute mechanical oscillations, and to receive the mechanical oscillations of the mechanically oscillatable unit and convert them into an electrical, received signal; and
 an electronics unit embodied to produce the exciter signal based on the received signal such that a predeterminable phase shift is present between the exciter signal and received signal,
 wherein the electronics unit is configured to alternately set at least a first phase shift and a second phase shift at a time interval, to ascertain both a first frequency and a second frequency corresponding to the first phase shift and the second phase shift, respectively, and to calculate the density and viscosity of the medium independently of each other using the first frequency and the second frequency,
 wherein the density of the medium is calculated using a first analytical formula and the viscosity of the medium is calculated using a second analytical formula, and
 wherein the first phase shift essentially amounts to +90° or −90° and the second phase shift essentially to +45° or −135°, wherein the first phase shift of essentially +90° corresponds to the second phase shift of essentially +45°, and wherein the first phase shift of essentially −90° corresponds to the second phase shift of essentially −135°.

2. The vibronic sensor of claim 1, wherein the oscillatable unit is arranged in a defined position within the container such that it extends to a determinable immersion depth in the medium.

3. The vibronic sensor of claim 1, wherein the electronics unit is configured to determine and/or to monitor a predetermined fill level of the medium in the container.

4. The vibronic sensor of claim 1, wherein the oscillatable unit is a membrane, single rod or oscillatory fork.

5. The vibronic sensor of claim 1, wherein the driving/receiving unit includes a piezoelectric element.

6. The vibronic sensor of claim 1, wherein the driving/receiving unit is an electromagnetic driving/receiving unit.

7. The vibronic sensor of claim 1, wherein the first analytical formula and the second analytical formula are each based on a solution of an equation of motion for an oscillatory movement of the oscillatable unit, the equation of motion including interaction of the oscillatable unit with the medium in the form of a compressive force and a frictional force, which arise from the medium surrounding the oscillatable unit, and as a frictional force that arises from an equally formed movement of the oscillatable unit within the medium.

8. The vibronic sensor of claim 1, wherein the first analytical formula is:

$$\rho = -\frac{T_2 + T_6 + \sqrt{T_3 + T_4}}{\hat{B}_a T_5},$$

and the second analytical formula is:

$$\eta = \frac{T_1 + \omega_{135}\left(T_2 - \sqrt{T_3 + T_4}\right)}{\hat{C}_a T_5},$$

wherein:

$T_1 = -2\hat{B}_a \hat{C}_a \omega_{90}^2 (\gamma \omega_{135} \omega_{90}^2 + D_r(T)(-\omega_{135}^2 + \omega_{90}^2))$, $T_2 = \hat{A}_a^2 D_r(T) \omega_{90}^3 - \hat{A}_a^2 \gamma \omega_{135} \omega_{90}^3 - \hat{A}_a^2 \Theta \omega_{135}^2 \omega_{90}^3$, $T_3 = \hat{A}_a^2 \omega_{90}^3 \hat{A}_a^2 (D_r(T) + \omega_{135}(\gamma - \Theta \omega_{135}))^2 \omega_{90}^2$, $T_4 = \hat{A}_a^2 \omega_{90} 4 \hat{B}_a \hat{C}_a \omega_{135}(D_r(T) - \Theta \omega_{90}^2)(-\gamma \omega_{135} \omega_{90}^2 + D_r(T)(\omega_{135}^2 - \omega_{90}^2))$, $T_5 = 2\omega_{135} \omega_{90}^3 (-\hat{A}_a^2 \omega_{135} + \hat{B}_a \hat{C}_a \omega_{90})$, and $T_6 = 2\hat{B}_a \hat{C}_a \omega_{135} \omega_{90}^2 (-D_r(T) + \Theta \omega_{90}^2)$, wherein $\Theta$ is the mass moment of inertia of the oscillatory rods of the oscillatable unit in the state not covered by medium,
wherein $\omega_0$ is the angular frequency of the oscillatable unit in the undamped case,
wherein $D_r(T)$ is the temperature dependent torsional stiffness of the oscillatable unit,
wherein $\gamma$ is the damping of the oscillatable unit not covered with medium,
wherein $\hat{A}_a$, $\hat{B}_a$, and $\hat{C}_a$ are geometry dependent parameters, and
wherein $\omega_{90}$ is the first frequency corresponding to the first phase shift of essentially +/−90°, and $\omega_{135}$ is the second frequency corresponding to the second phase shift of essentially 45° or −135° between the exciter signal and the received signal.

9. A method for determining density and/or viscosity of a medium in a container using a vibronic sensor, the method comprising:
 providing a vibronic sensor including a mechanically oscillatable unit, a driving/receiving unit, and an electronics unit;

exciting the oscillatable unit using the driving/receiving unit to execute mechanical oscillations using an electrical exciter signal produced by the electronics unit;

receiving and converting the mechanical oscillations of the mechanically oscillatable unit into an electrical, received signal using the driving/receiving unit, wherein the exciter signal is produced starting from the received signal such that a predeterminable phase shift is present between the exciter signal and the received signal;

using the electronics unit, alternately setting at least a first phase shift and a second phase shift at a time interval;

ascertaining both a first frequency and a second frequency corresponding to the first phase shift and the second phase shift, respectively;

calculating the density of the medium from the first frequency and the second frequency using a first analytical formula; and calculating the viscosity of the medium, independently of the density, from the first frequency and the second frequency using a second analytical formula, wherein the first phase shift is set to essentially +90° or −90° and the second phase shift to essentially +45° or −135°, wherein the first phase shift of essentially +90° corresponds to the second phase shift of essentially +45°, and wherein the first phase shift of essentially −90° corresponds to the second phase shift of essentially −135°.

10. The method of claim 9, the method further comprising:
monitoring a predetermined fill level of the medium in the container.

11. The method of claim 9, wherein that the first analytical formula and/or the second analytical formula are each based on a solution of an equation of motion for an oscillatory movement of the oscillatable unit, the equation of motion including interaction of the oscillatable unit with the medium as expressed as a compressive force and a frictional force, which result from the medium surrounding the oscillatable unit, and as a frictional force that arises as a result of an equally formed movement of the oscillatable unit within the medium.

12. The method of claim 9, wherein the first analytical formula is $$\rho = -\frac{T_2 + T_6 + \sqrt{T_3 + T_4}}{\hat{B}_a T_5},$$

and second analytical formula is $$\eta = \frac{T_1 + \omega_{135}(T_2 - \sqrt{T_3 + T_4})}{\hat{C}_a T_5},$$

wherein $T_1 = -2\hat{B}_a\hat{C}_a\omega_{90}^2(\gamma\omega_{135}\omega_{90}^2 + D_r(T)(-\omega_{135}^2 + \omega_{90}^2))$, $T_2 = \hat{A}_a^2 D_r(T)\omega_{90}^3 - \hat{A}_a^2\gamma\omega_{135}\omega_{90}^3 - \hat{A}_a^2\Theta\omega_{135}^2\omega_{90}^3$, $T_3 = \hat{A}_a^2\omega_{90}^3\hat{A}_a^2(D_r(T) + \omega_{135}(\gamma - \Theta\omega_{135}))^2\omega_{90}^2$, $T_4 = \hat{A}_a^2\omega_{90}4\hat{B}_a\hat{C}_a\omega_{135}(D_r(T) - \Theta\omega_{90}^2)(-\gamma\omega_{135}\omega_{90}^2 + D_r(T)(\omega_{135}^2 - \omega_{90}^2))$, $T_5 = 2\omega_{135}\omega_{90}^3(-\hat{A}_a^2\omega_{135} + \hat{B}_a\hat{C}_a\omega_{90})$, and $T_6 = 2\hat{B}_a\hat{C}_a\omega_{135}\omega_{90}^2(-D_r(T) + \Theta\omega_{90}^2)$, wherein $\Theta$ is the mass moment of inertia of the oscillatory rods of the oscillatable unit in the state not covered by medium, wherein $\omega_0$ is the angular frequency of the oscillatable unit in the undamped case, wherein $D_r(T)$ is the temperature dependent torsional stiffness of the oscillatable unit, wherein $\gamma$ is the damping of the oscillatable unit not covered with medium, wherein $\hat{A}_a$, $\hat{B}_a$ and $\hat{C}_a$ are geometry dependent parameters, and wherein $\omega_{90}$ is the first frequency corresponding to the first phase shift of essentially +/−90°, and $\omega_{135}$ is the second frequency corresponding to the second phase shift of essentially 45° or −135° between the exciter signal and the received signal.

* * * * *